United States Patent [19]

Daly et al.

[11] 4,451,687

[45] May 29, 1984

[54] CATALYST FOR THE HYDRODEALKYLATION OF ALKYLAROMATIC COMPOUNDS

[75] Inventors: Francis P. Daly, Haddonfield, N.J.; Frederick C. Wilhelm, West Chester, Pa.

[73] Assignee: Air Products and Chemicals, Inc., Allentown, Pa.

[21] Appl. No.: 540,214

[22] Filed: Oct. 7, 1983

Related U.S. Application Data

[62] Division of Ser. No. 395,192, Jul. 6, 1982.

[51] Int. Cl.$^3$ ............................................... C07C 3/58
[52] U.S. Cl. ..................................................... 585/489
[58] Field of Search ......................................... 585/489

[56] References Cited

U.S. PATENT DOCUMENTS

| | | | |
|---|---|---|---|
| 2,692,293 | 10/1954 | Heinemann | 585/489 |
| 2,773,917 | 12/1956 | Coonradt et al. | 585/489 |
| 2,951,886 | 9/1960 | Paulson | 585/489 |
| 3,178,486 | 4/1965 | Maerker et al. | 585/489 |
| 3,277,197 | 10/1966 | Notari | 585/489 |
| 3,560,584 | 2/1971 | Duhaut et al. | 252/465 |
| 3,760,023 | 10/1973 | Patrick et al. | 585/489 |
| 3,900,430 | 8/1975 | Beaty | 252/463 |
| 3,992,486 | 11/1976 | Cosyns et al. | 585/489 |

*Primary Examiner*—Curtis R. Davis
*Attorney, Agent, or Firm*—Michael Leach; E. Eugene Innis; James C. Simmons

[57] ABSTRACT

An alkylaromatic hydrocarbon feed stream is hydrodealkylate in the presence of a catalyst having a reduced rate of deactivation, or a lower coking tendency. The catalyst comprises a gamma-alumina support containing 8 to 12 wt.% $Cr_2O_3$ and 0.2 to 0.7 wt.% $Na_2O$ and having a surface area from 175 to 275 $m^2/g$ and a pore volume from 0.5 to 1.2 cc/g. The catalyst is also useful in the hydrodesulfurization of thiophene containing hydrocarbon streams.

10 Claims, No Drawings

CATALYST FOR THE HYDRODEALKYLATION OF ALKYLAROMATIC COMPOUNDS

This is a division of application Ser. No. 395,192, filed July 6, 1982.

TECHNICAL FIELD

The invention relates to the catalytic hydrodealkylation of alkylaromatics of the parent aromatic hydrocarbons. More specifically, the invention relates to a process for the hydrodealkylation of alkylbenzenes such as toluene to afford benzene as the product.

BACKGROUND OF THE INVENTION

The hydrodealkylation of alkylaromatic hydrocarbons has been practiced for many years. The principal process involves the conversion of toluene and similar alkyl substituted benezenes to benzene. Such processes may be catalytic or non-catalytic in nature. Most commercial catalytic processes employ chromia or magnesia deposited on an alumina base as the catalyst. Such catalysts for the hydrodealkylation of alkylaromatic feedstocks, for example the production of benzene from pyrolysis gasoline, tend to deactivate with use, presumably due to coke deposition on the catalyst surface. Therefore, measuring the amount of coke and the rate at which it is deposited provides a means for determining the deactivation of the catalyst.

In addition, commercial catalytic hydrodealkylation processes may use a chromia on alumina catalyst because, unlike noble metal catalysts, this catalyst is not readily susceptible to sulfur poisoning; rather it acts as a hydrodesulfurization catalyst. This aspect is advantageous since thiophene which is usually present in alkylaromatic feed streams is difficult to separate from benzene.

It is believed that acid sites promote polymerization of either hydrogenolysis products or aromatic hydrocarbons resulting in hydrocarbon condensation on the catalyst surface. Under the conditions of the process these condensed species are dehydrogenated forming coke. The result of these reactions is a reduction in activity of the catalyst since the coke is strongly adsorbed onto the sites which promote dealkylation. In other words, this coke or carbon build-up either blocks or poisons the active catalyst sites causing deactivation.

Since a chromia on alumina catalyst suffers gradual deactivation due to coking under hydrodealkylation conditions, the reactor temperature must gradually be increased to maintain an acceptable level of conversion. Typically, when the conversion level drops below about 50% at 1200° F. (649° C.), the catalyst is regenerated. The normal cycle life may be four to six months with high coking feedstocks such as pyrolysis gasoline. Initial catalyst activity decreases with regeneration until eventually the catalyst can no longer be used due to either low activity or thiophene breakthrough.

Therefore, a catalyst which is more deactivation-resistant, or demonstrates a decreased rate of coke formation, would permit greater efficiency in the hydrodealkylation process by converting toluene to benzene at a greater rate for a longer period of time before the catalyst must be regenerated. In addition, the catalyst still must provide commercially acceptable conversion rates at an acceptable selectivity.

U.S. Pat. No. 2,692,293 discloses the selective dealkylation of alkyl substituted aromatic hydrocarbons to lower molecular weight aromatic hydrocarbons using a supported catalyst which comprises an inactive carrier having a surface area generally in excess of 50 $m^2/g$ and containing less than about 15 wt% of a catalytic dehydrogenative material such as the metals of Group VIa including molybdenum and chromium oxides, and noble metals of the platinum-palladium group. The inactivation of the catalyst carrier material is effected by introducing into the carrier material an alkaline earth compound or an alkali metal oxide at about 0.1 to 2 wt% based on the carrier. Such deactivation is said to minimize the occurrence of side reactions which tend to produce coke and other products.

U.S. Pat. No. 2,773,917 discloses demethylation of methyl-substituted benzenes with a catalyst comprising chromia or molybdena composited with a suitable carrier. Although 4 to 12 wt% chromia supported on an alumina catalyst is suggested, only a co-precipitated chromia-alumina catalyst is shown in the examples. It is stated that maximum yield with a minimum of coke formation can be achieved by varying the reaction conditions within specified ranges.

U.S. Pat. No. 2,951,886 discloses the recovery of sulfur-free nitration grade benzene from crude coke oven or coal tar light oils by dealkylating in the presence of hydrogen at temperatures above 1200° F. in the presence of a catalyst consisting of approximately 10 through 15 wt% chromium oxide on a high purity, low sodium content, gamma type alumina support. The process is said to proceed with little or no coking affect.

U.S. Pat. No. 3,277,197 discloses a hydrodealkylation process employing oxides or sulfides of the metals of Group VIb supported on alumina of high purity, preferably in the eta phase, characterized by an elevated porosity, a surface area of about 150 to 200 $m^2/g$ and an average diameter of the pores of more than 150 Angstroms and less than 550 Angstroms.

U.S. Pat. No. 3,760,023 discloses a process for the hydrodealkylation of alkyl substituted aromatic hydrocarbons with a catalyst comprising a metal of Group VIb in an amount of about 5 to 15 wt% of the finished catalyst and 1 to 10 wt% of a promoter selected from the group consisting of alkali metals, alkaline earth metals and rare earth metals. The active metal and the promoter are deposited on an inert oxide support which preferably includes a high area alumina having a boehmite, bayerite, beta, or eta crystalline form, or other aluminas, silica-aluminas, silica, silica-magnesia, silica-zirconia, alumina-magnesia, etc.

U.S. Pat. No. 3,900,430 discloses a process for converting hydrocarbon oils to desirable components by contacting the oils in the presence of hydrogen under hydrocarbon conversion conditions with a catalyst comprising a catalytic amount of a catalytic material supported on gamma alumina prepared by a specific process and having a surface area from about 225 to about 400 $m^2/g$. Different groupings of catalytic metals are disclosed for reforming light hydrocarbon stocks to produce gasoline, benzene and the like, for hydrosulfurizing hydrocarbon oils, and for dehydrogenating hydrocarbon oils using the described alumina as the support.

U.S. Pat. No. 3,992,468 in comparative Example 1B shows a hydrodealkylation process using a conventional hydrodealkylation catalyst containing 7.5% of chromium oxide deposited on alumina having a specific surface of 170 $m^2/g$, a pore volume of 0.60 cc/g.

SUMMARY OF THE INVENTION

A catalyst has been discovered for use in the hydrodealkylation of alkylaromatic hydrocarbons to the parent aromatic hydrocarbon. The alkylaromatic hydrocarbon feed stream is contacted with hydrogen under hydrodealkylation conversion conditions in the presence of a catalyst comprising a gamma-alumina support impregnated with about 8 to 12 wt% chromium oxide ($Cr_2O_3$) and about 0.2 to 0.7 wt% sodium oxide ($Na_2O$). The resulting catalyst has a surface area from 175 to 275 $m^2/g$ and a pore volume from 0.5 to 1.2 cc/g. Generally, the hydrodealkylation process is performed at a temperature from 500° to 700° C., a pressure from 30 to 70 atm and a hydrogen:hydrocarbon molar ratio from 2:1 to 15:1.

The catalyst of the invention has a significantly reduced rate of deactivation compared to a comparable commercial catalyst, based on its lower coking tendency. The catalyst acquires substantially less coke on either a unit volume or a unit surface area basis than the commercial catalyst while maintaining comparable conversion rates and selectivity.

In another embodiment of the invention there is provided a process for the hydrodesulfurization of a hydrocarbon gas stream containing thiophene or other sulfur organic materials by contacting the gas stream with hydrogen in the presence of the catalyst of the invention at hydrodesulfurization conditions, such as a temperature from 500° to 700° C., a pressure from 30 to 70 atm. and a hydrogen-hydrocarbon molar ratio from 2:1 to 15:1.

The catalyst demonstrates good hydrodesulfurization capability in that it can remove thiophene to a level of about 1 ppm or less in a hydrocarbon industrial gas stream.

In addition to the reduced deactivation rate the catalyst in hydrodealkylation service offers the following additional features:

The benzene product purity from the demethylation of toluene is comparable to that of a commercial catalyst.

The catalyst has a crush strength of about 2.7 to 3.0 lb/mm which makes it suitable for fixed bed catalytic operation.

The catalyst is capable of regeneration after deactivation substantially without activity or selectivity loss through at least one cycle.

DETAILED DESCRIPTION OF THE INVENTION

A catalyst has been discovered for the hydrodealkylation of alkylaromatic hydrocarbons to aromatic hydrocarbons, for example, toluene to benzene, which catalyst manifests greater resistance to deactivation while maintaining good conversion and selectivity levels. The catalyst uses as a carrier, or support, a low density gamma-alumina having a surface area of about 250 to 350 $m^2/g$. This high surface area, low density gamma-alumina is impregnated with 8 to 12 wt% $Cr_2O_3$ and 0.2 to 0.7 wt% $Na_2O$. It is preferred that the chromia level range from 8.5 to less than 10, especially about 9 wt%. The preferred loading of sodium oxide ranges from 0.3 to 0.6 wt%, ideally about 0.4 wt%. The final catalyst should possess a pore volume in the range from 0.5 to 1.2 cc/g, preferably 0.6 to 0.9 cc/g and a surface area in the range of 175 to 275 $m^2/g$.

The hydrodealkylation process is performed by contacting the aklylaromatic hydrocarbon gas stream with hydrogen in the presence of the chromia and sodium oxide impregnated gamma-alumina catalyst of the invention at a hydrogen:hydrocarbon molar ratio ranging from 2:1 to 15:1, preferably about 3:1 to 6:1, at a liquid hourly space velocity of about 0.3 $hr^{-1}$ to 1.5 $hr^{-1}$ under typical hydrodealkylation conditions for a time sufficient to effect the generation of the desired dealkylated aromatic hydrocarbon products.

Suitable process temperatures range from about 500° to 700° C., preferably 570° to 650° C., and suitable pressures range from about 30 to 70 atm, preferably 50 to 60 atm.

The chromia loading is critical to the stability, or resistance to deactivation, of the catalyst. The sodium oxide level is important to the dealkylated aromatic hydrocarbon selectivity, e.g. benzene selectivity from the conversion of toluene. An increase in the sodium oxide level appears to reduce toluene conversion but increases benzene selectivity.

Contemplated as the functional, or operative, equivalent of sodium oxide in this invention are other alkali or alkaline earth metal oxides, for example, $Li_2O$, $K_2O$, MgO, CaO and the like, in amounts of about 0.1 to 2.0 wt% based on the carrier.

The hydrodealkylation catalysts employed in the practice of the invention can be prepared by techniques known in the art for the preparation of similar catalyst systems.

A suitable procedure for preparing the catalysts of the invention would include the following steps. A gammma-alumina support material having a surface area from 250 to 350 $m^2/g$ is mixed with water with or without a pore forming agent such as Methocel F4M cellulose ether, extruded and dried at about 250° F. (121° C.). The dried extruded pellets are then treated in dry air at about 1050° F. (566° C.).

Chromia and sodium oxide impregnation may be performed through batch processing by the "excess solution" technique. This technique involves completely immersing a weighed amount of pellets in a vessel containing a solution having the proper concentration of chromic acid ($CrO_3$) and sodium hydroxide (NaOH). Since this chromic acid- and sodium hydroxide-containing solution determines the amount of chromia and sodium oxide in the finished catalyst, the actual concentration of each component can only be determined after evaluation of the intermediate alumina extrudate. Following the soak, the excess solution is drained off and the catalyst is dried at about 250° F. (121° C.) in a forced air oven. Finally, the dried pellets are calcined at about 1000° F. (538° C.) in flowing dry air.

In addition to impregnating by immersion, the pellets can also be impregnated by spraying with the chromic acid-sodium hydroxide solution.

A suitable gamma-alumina support material for preparing the above-described hydrodealkylation catalyst is low density alpha-alumina monohydrate (boehmite), for example, Kaiser Chemical Substrate Alumina (KCSA) support material marketed by Kaiser Chemical Company.

The following examples are intended to be illustrative of the invention without being limitative.

EXPERIMENTAL

The methodology used in evaluating the different catalysts was the following:

1. The fresh catalysts were tested for toluene hydrodealkylation activity, thiophene hydrodesulfurization activity, and benzene selectivity using feedstock compositions and operating conditions as designated in the Examples.
2. In a second test unit, fresh catalysts were subjected to an accelerated coking test, achieved through feedstock adjustment, for approximately 80 hr, using designated feedstock compositions and operating conditions.
3. The coked catalysts were then tested for toluene hydrodealkylation activity, thiophene hydrodesulfurization activity and benzene selectivity in the same manner in which the fresh catalysts were tested.
4. The coked catalysts were then regenerated in the second test unit.
5. The regenerated catalysts were then tested for toluene hydrodealkylation activity, thiophene hydrodesulfurization activity and benzene selectivity in the same manner as the fresh catalyst.

CATALYST ACTIVITY TEST

The function of each catalyst (fresh, coked and regenerated) for toluene hydrodealkylation activity, thiophene hydrodesulfurization activity and benzene selectivity was measured in a fixed bed, down flow catalyst test unit. For each test, the reactor was a $\frac{3}{8}''$ schedule 40 stainless steel pipe charged with 35 cc of catalyst.

ACCELERATED COKING TEST

The accelerated coking tests were performed in either the catalyst activity test unit or a specialty catalyst pilot unit (SCS unit). The SCS unit consists of 4 separate reactor systems which allow 4 separate catalysts to be coked simultaneously. Each reactor has its own feed, gas metering and liquid product collection system. The effluent gas streams, however, are combined in one pressure controller which determines the pressure in all 4 reactors. The unit was equipped with oxygen and nitrogen supply systems for in situ catalyst regeneration.

Each reactor was a $\frac{3}{4}''$ schedule 80 stainless steel pipe, approximately 32" in length having either 1 or 3 side-entering thermowells in the lower half. The reactors are inserted into 4 vertical holes in a reactor heating block. The block is equipped with 3 zone heating loops, in the top, middle and bottom. Seventy-five cc of catalyst were loaded into each reactor on top of 35 cc of tabular alumina (alpha-$Al_2O_3$). The remaining reactor void (110 cc) was also filled with tabular alumina. This section served as a reactant preheater.

Under normal commercial operating conditions, a commercial chromia-on-alumina catalyst, for example, may lose one-half of its hydrodealkylation activity in 4 to 6 months accompanied by a 20 wt% increase in coke on the catalyst surface. The coking test was designed to simulate this coking process, in an accelerated mode. The duration of the test was set at about 80 hr using designated feedstock compositions and operating conditions.

CATALYST REGENERATION

The SCS unit was used also to regenerate coke catalysts. Each reactor was loaded with 35 cc of coke catalyst. Catalysts in two reactors were regenerated simultaneously on a staggered schedule as follows:

1. At 800° F. (427° C.), 1.47 vol % oxygen in nitrogen was introduced to the catalyst bed at a gas hourly spaced velocity (GHSV) of 17,000 $hr^{-1}$.
2. The reactor temperature was increased to 1000° F. (538° C.) maintaining the same gas flow rate.
3. As the rate of coke burn-off decreased, as determined by gas chromatographic analysis of the vent gas, the temperature was increased to 1100° F. (593° C.).
4. As the burn-off rate decreased at 1100° F. (593° C.), the oxygen content of the feed gas was increased to 2.47 vol % and the GHSV was decreased to 9000 $hr^{-1}$.

EXAMPLE 1

This example shows preparation of a hydrodealkylation catalyst of the invention. 6.8 kg of a low density alpha-alumina monohydrate (boehmite) were charged to a high shear mixer along with 99.5 g of Methocel F4M cellulose ether. The materials were dry mixed for 5 min and then for an additional 30 min with 5.4 l deionized water. The mixture was then extruded using a die plate with $\frac{1}{8}''$ holes. The extrudate was dried at 250° F. (121° C.) for about 2 hours. The dried pellets were then heated to 1050° F. (566° C.) in dry flowing air for about 2 hours.

Impregnation was performed using 0.5 l of the calcined substrate. The substrate was immersed in a solution (0.5 l) containing 43.3 g chromic acid and 2.1 g sodium hydroxide pellets. The substrate remained totally immersed in the chromic acid/sodium hydroxide solution for about 30 minutes at room temperature after which the pellets were drained for about 15 minutes and subsequently dried at 250° F. (121° C.). The impregnated dried pellets were then subjected to a second calcination at 1000° F. (538° C.) in flowing dry air for about 2 hours. The yield of hydrodealkylation catalyst 1 was 208 g possessing the physical properties shown in Table 1.

Catalysts 2-9 were prepared using the same general procedure varying the alumina phase substrate, calcination conditions and the concentration of the chromic acid and sodium hydroxide in the impregnating solution. The gamma-alumina support used for catalyst 2 was a higher density gamma alumina marketed as Catapal SB alumina substrate by Conoco. The alumina support for catalysts 3-9 was eta-alumina prepared from beta-alumina trihydrate (bayerite). Table 1 contains physical data for catalysts 1-9.

TABLE 1

| | CATALYST | | | | | | | | |
|---|---|---|---|---|---|---|---|---|---|
| | 1 | 2 | 3 | 4 | 5 | 6 | 7 | 8 | 9 |
| Alumina Phase | gamma | gamma | eta | eta | eta | eta | eta | eta | eta |
| $Cr_2O_3$ (wt %) | 9.2 | 19.0 | 18.85 | 10.84 | 5.78 | 5.78 | 5.78 | 5.78 | 18.1 |
| $Na_2O$ (wt %) | 0.27 | 0.44 | 0.43 | 0.26 | 0.32 | 0.32 | 0.32 | 0.32 | 0.53 |
| Density (g/ml) | 0.46 | — | — | — | — | — | — | — | 1.06 |
| Crush Strength (lb/mm) | 5.18 | — | — | — | — | — | — | — | 4.74 |
| Surface Area | 255 | 99 | 256 | 329 | 343 | 253 | 176 | 110 | 88 |

TABLE 1-continued

| | CATALYST | | | | | | | | |
|---|---|---|---|---|---|---|---|---|---|
| | 1 | 2 | 3 | 4 | 5 | 6 | 7 | 8 | 9 |
| ($m^2/g$) | | | | | | | | | |
| Pore Volume (cc/g) | 0.88 | — | 0.29 | 0.33 | 0.35 | 0.35 | 0.38 | 0.40 | 0.26 |
| Pore Size Distribution (%) | | | | | | | | | |
| <70 Å | 10.7 | — | 38.0 | 46.5 | 51.4 | 48.8 | 36.0 | 24.7 | 18.6 |
| 70–580 Å | 72.0 | — | 23.4 | 13.6 | 16.4 | 23.3 | 35.0 | 46.6 | 61.8 |
| >580 Å | 17.3 | — | 38.6 | 39.9 | 32.2 | 27.9 | 29.0 | 28.7 | 19.6 |
| Pore Diameter at Half Volume (Å) | ~125 | — | — | — | — | — | — | — | — |
| Calcination Conditions | | | | | | | | | |
| °F. | 1000 | 1400 | 1000 | 1000 | 1000 | 1200 | 1400 | 1400 | 1400 |
| Hours | 2 | 4 | 2 | 2 | 2 | 2 | 2 | 8 | 4 |
| Atmosphere | a | b | a | a | a | a | a | b | b |

$^a$Dry air
$^b$20% steam, 80% air

EXAMPLE 2

The initial values for toluene hydrodealkylation, benzene selectivity and thiophene hydrodesulfurization were determined for catalysts 1–9 using a gas stream having the following composition and under the following operating conditions:

| Feed Compositions (wt %) | | Operating Conditions | |
|---|---|---|---|
| Benzene | 0.5 | Temperature (°F.) | 1100 |
| Toluene | 99.0 | Pressured (psig) | 800 |
| Thiophene | 0.5 | H$_2$/Hydrocarbon (molar) | 5.0 |
| | | LHSV (hr$^{-1}$) | 0.76 |

Table 2 presents the toluene hydrodealkylation activity, benzene selectivity and thiophene hydrodesulfurization activity for the fresh catalysts.

The catalysts were then subjected to a modified accelerated coking test under the designated conditions using a hydrocarbon gas stream containing the following gaseous components:

| | Accelerated Coking Test | |
|---|---|---|
| | A | B |
| Feed Composition (wt) | | |
| Cyclohexene | 1.5 | 1.0 |
| Cyclohexane | 6.3 | 6.8 |
| n-Heptane | 6.0 | 6.0 |
| Benzene | 33.0 | 30.0 |
| Toluene | 30.0 | 35.0 |
| Xylenes | 6.0 | 8.5 |
| Ethyl Benzene | 5.0 | 7.0 |
| Styrene | 3.0 | 1.0 |
| Cumene | 7.5 | 3.5 |
| Indene | 1.5 | 1.0 |
| Pyridine | 0.2 | 0.2 |
| Operating Conditions | | |
| Temperature (°F.) | 1150 | 1100 |
| Pressure (psig) | 800 | 800 |
| H$_2$/Hydrocarbon (molar) | 2.0 | 2.0 |
| LHSV (hr$^{-1}$) | 1.47 | 1.47 |

The activities for the coked catalysts 1–9 were then redetermined and are presented in Table 2.

TABLE 2

| | CATALYST | | | | | | | | | | | |
|---|---|---|---|---|---|---|---|---|---|---|---|---|
| | 1 | 1 | 2 | 3 | 4 | 5 | 6 | 7 | 8 | 9 | 9 | 9 |
| Fresh Catalyst | | | | | | | | | | | | |
| Toluene Conversion (%) | 54.22 | 54.22 | 53.46 | 64.37 | 65.75 | 64.14 | 65.55 | 63.83 | 54.86 | 54.38 | 54.38 | 54.38 |
| Benzene Selectivity (mole %) | 90.69 | 90.69 | 93.99 | 86.36 | 85.08 | 82.36 | 86.92 | 84.03 | 91.18 | 93.37 | 93.37 | 93.37 |
| Coked Catalyst | | | | | | | | | | | | |
| Accelerated Coking Test | B | B | A | B | B | B | B | B | B | B | B | B |
| Toluene Conversion (%) | 49.63 | 49.54 | 6.91 | 55.08 | 51.65 | 49.58 | 52.01 | 46.16 | 33.93 | 42.28 | 39.52 | 16.00 |
| Benzene Selectivity (mole %) | 92.04 | 90.32 | 84.88 | 80.32 | 85.33 | 82.04 | 78.70 | 89.50 | 89.72 | 91.46 | 91.58 | 91.41 |
| Coke on Catalyst (wt %) | 6.7 | 7.2 | 36.9 | 4.6 | 10.6 | 7.9 | 9.9 | 11.0 | 10.5 | 5.0* | 7.1* | 19.8 |
| Coked vs Fresh Catalyst Δ% Toluene Conversion | −8.5 | −8.6 | −87 | −14.4 | −21.4 | −22.7 | −20.7 | −27.7 | −38.2 | −22.3 | −27.3 | −71 |
| Regenerated Catalyst | | | | | | | | | | | | |
| Toluene Conversion (%) | 55.7 | | | | | | | | | 51.2 | | |
| Benzene Selectivity (mole %) | 89.8 | | | | | | | | | 93.7 | | |
| Regenerated vs Fresh Catalyst Δ% Toluene Conversion | +2.7 | | | | | | | | | −5.9 | | |

The thiophene content in the product gas stream was < 1.0 ppm for each catalyst, fresh or coked.
*Submitted for coke analysis after testing Catalyst 9 may be used as the standard for making comparisons since it is a commercially used hydrodealkylation catalyst. Catalyst 9 contained 18.1 wt% Cr$_2$O$_3$ and 0.53 wt% Na$_2$O on an eta-alumina support and had a surface area of 88 m²/g and a pore volume of 0.26 cc/g.

Commercial catalyst 9 demonstrated 22.3 and 27.3% losses in hydrodealkylation activity for two separate accelerated coking test B experiments. Catalyst 1 which is a catalyst within the scope of the invention demonstrated losses in hydrodealkylation activity of only 8.5 and 8.6% in two test B experiments. This is equivalent to a loss in hydrodealkylation activity only about one-third that of the commercial catalyst. The initial toluene conversion activity and benzene selectivity of catalyst 1 was comparable to that of commercial catalyst 9.

Without being held to any particular theory, the reduction in the rate of deactivation for catalyst 1 compared to commercial catalyst 9 may be attributed to one or both of the following explanations. First, a change in the alumina phase from eta to gamma. Gamma is less acidic and acid sites promote polymerization of either hydrogenolysis products or aromatic hydrocarbons resulting in hydrocarbon condensation on the catalyst surface. These condensed species are dehydrogenated forming coke. The result of this coke formation is a reduction in activity since the coke is strongly adsorbed on sites which also promote dealkylation.

Second, as a result of the increased porosity and surface area of catalyst 1, a greater dispersion of $Cr_2O_3$ would be expected. This greater dispersion should result in the deactivation of fewer $Cr_2O_3$ sites upon build-up of a given amount of coke. Consequently, the overall activity of catalyst 1 decreases at a rate less than that of the lower porosity catalyst 9.

Catalyst 2 which had 19.0 wt% $Cr_2O_3$ and 0.44 wt% $Na_2O$ on a high density gamma-alumina with a 99 m²/g surface area lost 87% toluene conversion activity after the more severe accelerated coking test A. After the same coking test A, commercial catalyst 9 lost 71% activity indicating catalyst 2 was less stable.

While the toluene conversion activities of catalysts 3-7 were superior to that of the commercial catalyst 9, their benzene selectivities were significantly inferior.

Catalyst 4 contained $Cr_2O_3$ and $Na_2O$ levels within the ranges required for the catalyst of the invention. However, the surface area of the eta-alumina catalyst was greater and the pore volume less than the limits prescribed for the inventive catalyst. The initial activity of catalyst 4 was higher, but the loss of toluene conversion activity was comparable to catalyst 9. Eta-alumina catalyst 3, which was within the $Na_2O$ and surface area limits but outside the $Cr_2O_3$ and pore volume limits, showed a rate of deactivation less than catalyst 9 but more than 50% greater than catalyst 1. Catalysts 3 and 9 had comparable $Cr_2O_3$ and $Na_2O$ loadings on eta-alumina, but catalyst 3 had nearly three times the surface area.

Catalyst 8 had a toulene conversion activity and benzene selectivity comparable to catalysts 1 and 9 but showed considerable deactivation, i.e. a 38% loss in toluene conversion. Catalyst 8 which had an eta-alumina support was also outside the required ranges for $Cr_2O_3$, surface area and pore volume.

EXAMPLE 3

In this example experiments were conducted to insure that catalyst activity is not lost upon regeneration. Both catalyst 1 and commercial catalyst 9 were regenerated as described in the experimental section. The results are shown in Table 2. The toluene conversion activity of the regenerated commercial catalyst 9 was 51.2%, 5.9% less than its initial activity. The activity of the regenerated catalyst 1 was 55.7%, 2.7% higher than its initial activity. The benzene selectivities of the two regenerated catalysts are comparable to that of their initial values. Hydrodesulfurization activity was also the same with the thiophene content of the product being less than 1 ppm.

The physical properties of catalysts 1 and 9, both fresh and regenerated, are summarized in Table 3. The major differences in these catalysts which may contribute to the lower rate of deactivation for catalyst 1 of the invention are the following:

1. The support for catalyst 1 is a low density gamma-alumina. Catalyst 9 used an eta-alumina support.

2. The $Cr_2O_3$ loading for catalyst 1 is one-half that of catalyst 9, 9.2 versus 18.1 wt%. However, since catalyst activities were obtained using equal volumes of catalyst and the density of catalyst 1 is less than half that of commercial catalyst 9, the chromium oxide content on a catalyst volume basis is actually less than one-fourth that of the commercial catalyst.

3. The pore volume of catalyst 1 is over three times greater than that of catalyst 9, 0.88 versus 0.26.

4. The surface area of catalyst 1 is approximately three times greater than that of catalyst 9, 255 versus 88 m²/g.

TABLE 3

| Identity | Catalyst 1 | Catalyst 9 |
|---|---|---|
| Alumina Phase | gamma | eta |
| $Cr_2O_3$ (wt %) | 9.2 | 18.1 |
| $Na_2O$ (wt %) | 0.27 | 0.50 |
| Density (gm/ml) | 0.46 | 1.06 |
| Crush Strength (lbs/mm) | 5.18 | 4.74 |
| Surface Area (m²/gm) | | |
| Fresh | 255 | 88 |
| Regenerated | 199 | 91 |
| Pore Volume (ml/gm) | | |
| Fresh | 0.88 | 0.26 |
| Regenerated | 0.84 | 0.29 |
| Pore Size Distribution (%) | | |
| Fresh | | |
| <70 Å | 10.7 | 18.6 |
| 70-580 Å | 72.0 | 61.8 |
| >580 Å | 17.3 | 19.6 |
| Regenerated | | |
| <70 Å | 10.5 | 37.7 |
| 70-580 Å | 77.7 | 35.6 |
| >580 Å | 11.8 | 26.7 |
| Pore Diameter at Half Volume (Å) | | |
| Fresh | ~125 | ~109 |
| Regenerated | ~161 | ~94 |
| Description | ⅛" extrudate | ⅛" extrudate |

EXAMPLE 4

Another series of catalysts (10-15) were prepared in a manner similar to the procedure in Example 1 using low density gamma-alumina. Catalyst 16 was prepared by spraying the gamma-alumina support with the chromic acid/sodium hydroxide solution rather than by immersion. Catalysts 12 and 13 were prepared without Methocel F4M cellulose ether. Catalysts 10-16 are within the general scope of the invention.

Table 4 shows the physical properties of catalysts 10-16 as well as the toluene conversion activity and benzene selectivity values of catalysts 1, 9 and 10-16 which were determined using a feed gas stream as described in Example 2.

TABLE 4

| Catalyst | 1 | 9 | 10 | 11 | 12 | 13 | 14 | 15 | 16* |
|---|---|---|---|---|---|---|---|---|---|
| $Cr_2O_3$ (wt %) | 9.2 | 18.1 | 9.9 | 10.3 | 9.2 | 11.9 | 12.2 | 12.2 | 8.9 |
| $Na_2O$ (wt %) | 0.27 | 0.52 | 0.26 | 0.37 | 0.19 | 0.37 | 0.22 | 0.41 | 0.32 |
| Surface Area (m²/gm) | 255 | 88 | 258 | 254 | 237 | 227 | 243 | 234 | 224 |
| Pore Volume (cc/gm) | 0.88 | 0.26 | 0.77 | 0.77 | 0.89 | 0.91 | 1.00 | 0.86 | 0.89 |
| Toluene Conversion (%) | 65.8 | 64.9 | 62.5 | 67.9 | 68.4 | 67.9 | 71.1 | 70.8 | 64.3 |
| Benzene Selectivity (mole %) | 90.0 | 92.6 | 90.0 | 93.5 | 87.7 | 92.8 | 91.6 | 92.3 | 95.2 |

*Prepared by spray technique

Again, as can be seen in Table 4, catalyst 1 exhibited a lower benzene selectivity than that of commercial catalyst 9, 90.0 versus 92.6 mole %, respectively. It was suspected that this is a result of the lower sodium oxide content, 0.27 versus 0.53 wt%, respectively. Consequently, catalyst 10 was prepared as a second batch of catalyst comparable to catalyst 1 and catalyst 11 was prepared with a higher sodium oxide content. The results shown in Table 4 clearly demonstrate that higher sodium oxide loading promotes higher benzene selectivity; 90.0 mole % for catalyst 10 with 0.26 wt% sodium oxide versus 93.5 mole % for catalyst 11 with 0.37 wt% sodium oxide. In addition, catalyst 12 which was similar to catalyst 1 except for its lower sodium oxide content of about 0.2 wt% showed a lower benzene selectivity of 87.7 mole %. Catalysts 12–15 also demonstrate that higher sodium oxide content improves benzene selectivity.

In addition, these results suggest that the optional use of Methocel F4M pore forming agent in the preparation of the catalyst does not have a detrimental effect on catalyst activity or selectivity.

TABLE 5

| Catalyst | 9 | 9 | 13 | 15 |
|---|---|---|---|---|
| Fresh Catalyst | | | | |
| Toluene Conv. (%) | 64.9 | 64.9 | 67.9 | 70.8 |
| Benzene Sel. (mole %) | 92.6 | 92.6 | 92.8 | 92.3 |
| Coked Catalyst | | | | |
| Toluene Conv. (%) | 51.9 | 54.2 | 59.0 | 59.7 |
| Benzene Sel. (mole %) | 92.9 | 92.8 | 93.0 | 93.8 |
| Δ % Toluene Conv. | −20.0 | −16.5 | −13.1 | −15.6 |
| Thiophene (ppm) | <1 | <1 | <1 | <1 |

Catalysts 9, 13 and 15 were subjected to an accelerated coking test B of Example 2 for approximately 80 hr. The results presented in Table 5 show activity losses for the commercial catalyst 9 of about 17–20%. The catalysts of the invention (13 and 15) exhibited activity losses of about 13–16%, approximately three-fourths that of the commercial catalyst. This higher deactivation rate for catalysts 13 and 15 in comparison to catalyst 1 described in Table 2 is attributed to the higher chromia loading, approximately 12 wt% versus a 9.2 wt% for catalyst 1. The higher chromia loadings contributed to both higher initial activities and higher rates of deactivation. With a chromia level of 8.9 wt%, catalyst 16 had (Table 4) an initial activity of 64.3%. This is comparable to the value of 65.8 % for catalyst 1 with a 9.2 wt% chromia loading. When an initial activity value of 64.3% is used for catalysts 13 and 15, rather than those presented in Table 5, the losses in activity are 7–8%, comparable to that for catalyst 1.

Therefore, chromia loading is a critical element with regard to catalyst stability. Based on the experimental data, while a chromia level of 8 to 12 wt% is acceptable, the much preferred range for chromia on gamma-alumina support is 8.5 to less than 10 wt%, ideally about 9 wt%. Above 12 wt% chromia, catalyst deactivation rates are high and below 8 wt% chromia there is a significant loss of initial activity.

EXAMPLE 5

In this example another catalyst 18 within the scope of the invention is compared to another commercial catalyst 17 comprising chromia on an eta-alumina support. The catalysts were prepared by methods similar to that described in Example 1. Table 6 shows the properties of the two catalysts.

TABLE 6

| | 17 | 18 |
|---|---|---|
| Alumina Phase | eta | gamma |
| $Cr_2O_3$ (wt %) | 18.44 | 9.60 |
| $Na_2O$ (wt %) | 0.52 | 0.45 |
| Surface Area (m²/g) | 93.4 | 262 |
| Pore Volume (cc/g) | 0.31 | 0.74 |
| Bulk Density (g/cc) | 1.010 | 0.566 |
| Extrudate Diameter (inches) | 1/8 | 1/8 |

Accelerated deactivation (coking) was performed for each catalyst under the conditions cited in Table 7. In addition to the deactivation runs, the performance of each catalyst was determined using the standard activity test under the conditions also listed in Table 7. The activity tests were made on the fresh catalysts, on the coked catalysts after deactivation, and on the deactivated catalysts after subsequent regeneration. Thiophene breakthrough during the accelerated deactivation are shown as a function of hours on-stream in Table 8. The activity test results are detailed in Table 9.

TABLE 7

| TEST CONDITIONS | | |
|---|---|---|
| | ACCELERATED DEACTIVATION | STANDARD ACTIVITY |
| TEMPERATURE (°F.) | 1175 | 1150 |
| PRESSURE (psig) | 800 | 800 |
| H₂/Feed (molar) | 2.0 | 5.0 |
| LHSV (hr⁻¹) | 1.48 | 0.74 |
| PRE-HEATER* | Ambient | Ambient |
| FEED COMPOSITION (Wt %) | | |
| CYCLOHEXANE | 6.28 | — |
| CYCLOHEXANE | 1.51 | — |
| n-HEPTANE | 6.00 | — |
| BENZENE | 31.90 | — |
| TOLUENE | 29.80 | 99.5 |
| ETHYLBENZENE | 6.61 | — |
| XYLENES | 4.63 | — |
| STYRENE | 3.06 | — |
| CUMENE | 8.18 | — |
| INDENE | 1.08 | — |
| THIOPHENE | 6400 ppm | 5000 ppm |
| PYRIDINE | 1800 ppm | — |
| UNIDENTIFIED | 0.13 | — |

*Pre-heater temperature maintained at ambient for this project. At 1,000° F. the pre-heater lines fouled with coke after a few hours on stream.

TABLE 8

ACCELERATED DEACTIVATION RUN

| HOURS ON STREAM | Thiophene Breakthrough ppm | |
|---|---|---|
| | Catalyst 17 | Catalyst 18 |
| 4 | <1 | <1 |
| 12 | <1 | <1 |
| 36 | 2 | <1 |
| 60 | 140 | <1 |
| 64 | 228 | <1 |
| 68 | 280 | 2 |
| 72 | 440 | 3 |
| 76 | — | 4 |
| 84 | — | 6 |
| 92 | — | 20 |
| 104 | — | 40 |
| 112 | — | 95 |
| 120 | — | 153 |
| 128 | — | 190 |

TABLE 9

| | Catalyst 17 | Catalyst 18 |
|---|---|---|
| FRESH CATALYST | | |
| Toluene Conversion (wt %) | 67.72 | 69.62 |
| Benzene Selectivity (mole %) | 92.94 | 95.64 |
| Thiophene, Hour 3 (ppm) | <1 | <1 |
| COKED CATALYST* | | |
| Toluene Conversion (wt %) | 25.71 | 19.77 |
| Benzene Selectivity (mole %) | 96.86 | 106.8** |
| Thiophene, Hour 3 (ppm) | 1 | 14 |
| REGENERATED CATALYST | | |
| Toluene Conversion (wt %) | 68.3 | 61.0 |
| Benzene Selectivity (mole %) | 92.7 | 96.5 |
| Thiophene, Hour 3 (ppm) | <1 | <1 |

*Catalyst 17 - 74 hours of accelerated deactivation - 19.9 wt % coke; coking rate = 0.27 g coke/hr/cc catalyst. Rate of toluene conversion loss = 0.84 Δ %/hr.
Catalyst 18 - 128 hours of accelerated deactivation - 41.9 wt % coke; coking rate = 0.19 g coke/hr/cc catalyst. Rate of toluene conversion loss = 0.56 Δ %/hr.
**Selectivity value exceeds maximum allowable value as a result of inaccurate material balance.

From the Tables it can be seen that the inventive catalyst 18 exhibits a lower rate of deactivation and concurrent coke formation than catalyst 17, approximately ⅔ that of catalyst 17. More significantly, with respect to hydrodesulfurization activity, the accelerated deactivation run shows that after 60 hours on-stream commercial catalyst 17 exhibited a breakthrough of 140 ppm thiophene while catalyst 18 showed less than 1 ppm thiophene. Comparing the thiophene breakthrough for catalyst 17 and 18 at 72 hours on-stream, the numbers were 440 and 3, respectively. The data shows that catalyst 18 possessed a superior hydrodesulfurization activity life of approximately twice as long as commercial catalyst 17.

The data in Table 9 seems to indicate that catalyst 18 possessed inferior toluene conversion activity after accelerated deactivation (coking). This apparent inferiority is illusory because catalyst 17 was tested after only 74 hours of accelerated coking whereas catalyst 18 was tested after 128 hours of accelerated coking. Consequently, the rate of coke formation for catalyst 17 was 0.27 g/hr/cc catalyst while for catalyst 18 it was only 0.19 g/hr/cc catalyst. Also, the activity data indicates that catalyst 18 after a significantly longer deactivation period did not recover its initial activity after regeneration as did catalyst 17.

The following example compares the same commercial catalyst 17 with another catalyst within the scope of the invention after both had been subjected to an accelerated deactivation (coking) test for 74 hours.

EXAMPLE 6

The performance of commercial catalyst 17 and catalyst 19, which is within the scope of the invention, is compared. The activity tests were made on the fresh catalyst, the coked catalyst after deactivation, and the deactivated catalyst after subsequent regeneration. Importantly, both catalysts were subjected to accelerated coking for the same 74 hour period. Table 10 gives the physical properties of the catalysts and the activity data.

TABLE 10

ACTIVITY TEST RESULTS[1]

| | Catalyst 17 | Catalyst 19 |
|---|---|---|
| Alumina phase | eta | gamma |
| $Cr_2O_3$ (wt %) | 18.44 | 8.88 |
| $Na_2O$ (wt %) | 0.52 | 0.42 |
| Surface Area (m²/g) | 93.4 | 274 |
| Pore Volume (ml/g) | 0.31 | 0.69 |
| Bulk Density (g/cc) | 1.01 | 0.57 |
| Extrudate Diameter (inches) | ⅛ | ⅛ |
| FRESH CATALYST | | |
| Toluene Conversion (wt %) | 61.59 | 64.66 |
| Benzene Selectivity (mole %) | 97.19 | 102.08 |
| COKED CATALYST[2] | | |
| Toluene Conversion (wt %) | 49.31 | 61.10 |
| Benzene Selectivity (mole %) | 104.73 | 96.90 |
| REGENERATED CATALYST | | |
| Toluene Conversion (wt %) | 59.25 | 61.58 |
| Benzene Selectivity (mole %) | 98.05 | 97.13 |
| Fresh vs Coked Catalyst Δ % Toluene Conversion | −19.9 | −5.5 |
| Fresh vs Regenerated Catalyst Δ % Toluene Conversion | −3.8 | −4.7 |

[1]Values reported are average for four consecutive hours.
[2]74 hours accelerated coking It can be seen that the commercial catalyst after 74 hours of accelerated coking lost 19.9% of its toluene conversion activity compared to catalyst 19 which lost only 5.5% of its activity. After regeneration of the coked catalysts the commercial catalyst 17 showed a loss of 3.8% toluene conversion activity whereas catalyst 19 showed a loss of 4.7% in its activity. This example demonstrates the superior deactivation stability of the catalysts of the invention.

EXAMPLE 7

This example, in summary fashion, presents comparisons of the performance of four catalysts using the commercial catalyst 9 as the base case. The properties of the four catalysts discussed are described in Table 11. Table 12 presents the toluene conversion and benzene selectivity data for the fresh and coked catalysts. Table 12 also shows data relating to the accelerated coking test results. Table 13 presents the operating conditions of the accelerated deactivation tests which were different for different comparisons.

TABLE 11

| | 1 | 2 | 9 | 18 |
|---|---|---|---|---|
| Alumina Phase | gamma | gamma | eta | gamma |
| $Cr_2O_3$ (wt %) | 9.2 | 19.0 | 18.1 | 9.71 |
| $Na_2O$ (wt %) | 0.27 | 0.44 | 0.53 | 0.42 |
| Density (g/cc) | 0.461 | 0.84 | 1.06 | 0.57 |
| Surface Area (m²/g) | 255 | 99 | 88 | 259 |
| Pore Volume (cc/g) | 0.88 | 0.50 | 0.26 | 0.69 |
| Pore Size Distribution (%) | | | | |
| <70 Å | 10.7 | 2.8[1] | 18.6 | 7.9 |
| 70–580 Å | 72.0 | 83.2 | 61.8 | 82.5 |
| >580 Å | 17.3 | 14.0 | 19.6 | 9.6 |
| Pore Diameter at Half | ~125 | ~105 | ~109 | ~120 |

TABLE 11-continued

| | 1 | 2 | 9 | 18 |
|---|---|---|---|---|
| Volume (Å) | | | | |

[1] Porosity measurement made of the substrate, not the final catalyst

TABLE 12

| | 9[1] | 1[1] | 9[1] | 2[1] | 9[2] | 18[2] |
|---|---|---|---|---|---|---|
| Fresh Catalyst | | | | | | |
| Toluene Conversion (wt %) | 54.38 | 54.22 | 54.38 | 53.46 | 67.72 | 69.62 |
| Benzene Selectivity (mole %) | 93.37 | 90.69 | 93.37 | 93.99 | 92.94 | 95.64 |
| Coked Catalyst | | | | | | |
| Toluene Conversion (wt %) | 42.28 | 49.63 | 16.00 | 6.91 | 25.71 | 19.77 |
| Benzene Selectivity (mole %) | 91.46 | 92.04 | 91.41 | 84.88 | 96.86 | 100.00 |
| Accelerated Coking Test | | | | | | |
| Test | C | C | B | B | A | A |
| Duration (hr) | 79 | 79 | 79 | 79 | 74 | 128 |
| Wt % coke | 4.4 | 4.4 | 19.8 | 36.9 | 19.2 | 41.9 |
| Coking Rate (g coke/hr/cc catalyst) | 0.06 | 0.03 | 0.26 | 0.39 | 0.27 | 0.19 |

[1] Activity Test Conditions: 1100° F., 800 psig, 5.0 $H_2$: hydrocarbon (molar), LHSV = 0.76 $hr^{-1}$
[2] Activity Test Conditions: 1150° F., 800 psig, 5.0 $H_2$: hydrocarbon (molar), LHSV = 0.74 $hr^{-1}$

TABLE 13

ACCELERATED COKING TEST CONDITIONS

| | TEST A | TEST B | TEST C |
|---|---|---|---|
| FEED COMPOSITIONS (WT %) | | | |
| Cyclohexene | 1.5 | 1.5 | 1.0 |
| Cyclohexane | 6.3 | 6.3 | 6.8 |
| n-Heptane | 6.0 | 6.0 | 6.0 |
| Benzene | 32.7 | 33.0 | 30.0 |
| Toluene | 29.8 | 30.0 | 35.0 |
| Xylenes | 6.0 | 6.0 | 8.5 |
| Ethyl Benzene | 5.0 | 5.0 | 7.0 |
| Styrene | 3.0 | 3.0 | 1.0 |
| Cumene | 7.5 | 7.5 | 3.5 |
| Indene | 1.5 | 1.5 | 1.0 |
| Pyridine | 0.2 | 0.2 | 0.2 |
| Thiophene | 0.5 | — | — |
| OPERATING CONDITIONS | | | |
| Temperature (°F.) | 1175 | 1150 | 1100 |
| Pressure (psig) | 800 | 800 | 800 |
| $H_2$/hydrocarbon (molar) | 2.0 | 2.0 | 2.0 |
| LHSV, $hr^{-1}$ | 1.47 | 1.47 | 1.47 |

From the Tables it can be seen that catalyst 1 which had a low sodium oxide level of 0.27 yielded a lower benzene selectivity as compared to commercial catalyst 9 having a sodium oxide level of 0.53. Both catalysts 2 and 18 had higher sodium oxide loadings on gamma-alumina substrate and had benzene selectivities comparable to the commercial catalyst.

Both catalysts of the invention in which chromia and sodium oxide were impregnated into KCSA gamma-alumina substrate (catalysts 1 and 18) had coking rates approximately one-half that of the commercial catalyst 9 comprising an eta-alumina support. On the other hand, catalyst 2 which was prepared with Catapal gamma-alumina substrate material with a surface area of 99 $m^2/g$ had a coking rate approximately 1.5 times that of commercial catalyst 9.

As noted in Tables 12 and 13 the operating conditions of the accelerated coking tests were different. However, as the results in Table 12 reveal the rate of coke formation for catalyst 9 is comparable for both coking test A and B. Since the coking rate for catalyst 2 (Catapal substrate) is over 2.1 times that of catalyst 18 (KCSA substrate), it is reasonable to assume that the physical properties of the KCSA gamma-alumina are important in defining catalyst performance. Furthermore, it may be concluded that other gamma-alumina substrate materials may not be as effective for hydrodealkylation as a high surface area, low density KCSA gamma-alumina.

We claim:

1. A process for the hydrodealkylation of an alkylaromatic hydrocarbon to the aromatic hydrocarbon which comprises contacting an alkylaromatic hydrocarbon feed stream with hydrogen under hydrodealkylation conversion conditions in the presence of a catalyst comprising a gamma-alumina impregnated with about 8 to 12 wt% chromium oxide and about 0.3 to 0.6 wt% sodium oxide, the catalyst having a surface area from 175 to 275 $m^2/g$ and a pore volume from 0.05 to 1.2 cc/g.

2. The process of claim 1 wherein the chromium oxide is from 8.5 to less than 10 wt%.

3. The process of claim 1 wherein the pore volume is from 0.6 to 0.9 cc/g.

4. The process of claim 1 wherein the surface area of the gamma-alumina support prior to its impregnation with chromium oxide and sodium oxide has a surface area from 250 to 350 $m^2/g$.

5. The process of claim 1 wherein the alkyl-aromatic hydrocarbon is toluene and the aromatic hydrocarbon is benzene.

6. The process of claim 1 wherein the hydrodealkylation conversion conditions comprise a temperature from 500° to 700° C., a pressure from 30 to 70 atm. and a hydrogen:hydrocarbon mole ratio from 2:1 to 15:1.

7. A process for the hydrodemethylation of toluene to benzene which comprises contacting a toluene containing feed stream with hydrogen at a temperature from 570° to 650° l C., a pressure from 50 to 60 atm and a hydrogen:hydrocarbon mole ratio from 3:1 to 6:1 in the presence of a catalyst comprising about 8.5 to less than 10 wt% chromia and 0.3 to 0.6 wt% sodium oxide impreganted into a gamma-alumina support, the catalyst having a surface area from 175 to 275 $m^2/g$ and a pore volume from 0.6 to 0.9 cc/g.

8. The process of claim 1 wherein the chromium oxide is about 9 wt%.

9. The process of claim 3 wherein the chromium oxide is about 9 wt%.

10. The process of claim 2 wherein the sodium oxide is about 0.4 wt%.

* * * * *

UNITED STATES PATENT AND TRADEMARK OFFICE
CERTIFICATE OF CORRECTION

PATENT NO. : 4,451,687

DATED : May 29, 1984

INVENTOR(S) : Francis P. Daly and Frederick C. Wilhelm

It is certified that error appears in the above-identified patent and that said Letters Patent are hereby corrected as shown below:

Column 16, Line 27
    Delete "0.05" and substitute therefor -- 0.5 --

Signed and Sealed this

Twenty-third Day of October 1984

[SEAL]

Attest:

GERALD J. MOSSINGHOFF

Attesting Officer     Commissioner of Patents and Trademarks